(12) United States Patent
Khairkhahan

(10) Patent No.: US 7,175,656 B2
(45) Date of Patent: Feb. 13, 2007

(54) PERCUTANEOUS TRANSCATHETER HEART VALVE REPLACEMENT

(76) Inventor: Alexander Khairkhahan, 1105 Lincoln Ave., Palo Alto, CA (US) 94301

( * ) Notice: Subject to any disclaimer, the term of this patent is extended or adjusted under 35 U.S.C. 154(b) by 43 days.

(21) Appl. No.: 10/419,706

(22) Filed: Apr. 18, 2003

(65) Prior Publication Data
US 2004/0210307 A1 Oct. 21, 2004

(51) Int. Cl.
*A61F 2/24* (2006.01)
(52) U.S. Cl. ............. 623/1.26; 623/2.17; 606/200
(58) Field of Classification Search ......... 623/1.24, 623/1.26, 2.12–2.14, 2.17, 2.18, 2.38
See application file for complete search history.

(56) References Cited

U.S. PATENT DOCUMENTS

| | | | |
|---|---|---|---|
| 3,671,979 A | 6/1972 | Moulopoulos | |
| 3,874,388 A | 4/1975 | King et al. | |
| 4,007,743 A | 2/1977 | Blake | |
| 4,352,211 A | 10/1982 | Parravicini | |
| 4,994,077 A | 2/1991 | Dobben | |
| 5,332,402 A * | 7/1994 | Teitelbaum | 623/2.42 |
| 5,375,612 A * | 12/1994 | Cottenceau et al. | 128/899 |
| 5,397,351 A * | 3/1995 | Pavcnik et al. | 623/2.35 |
| 5,411,552 A * | 5/1995 | Andersen et al. | 623/2.18 |
| 5,413,599 A | 5/1995 | Imachi et al. | |
| 5,527,338 A * | 6/1996 | Purdy | 606/200 |
| 5,855,601 A | 1/1999 | Bessler et al. | |
| 5,957,949 A * | 9/1999 | Leonhardt et al. | 623/1.24 |
| 6,092,529 A * | 7/2000 | Cox | 128/898 |
| 6,142,987 A * | 11/2000 | Tsugita | 604/500 |
| 6,152,144 A * | 11/2000 | Lesh et al. | 128/898 |
| 6,287,334 B1 * | 9/2001 | Moll et al. | 623/1.24 |
| 6,296,662 B1 | 10/2001 | Caffey | |
| 6,299,637 B1 * | 10/2001 | Shaolian et al. | 623/1.24 |

(Continued)

FOREIGN PATENT DOCUMENTS

DE 4101935 A1 * 7/1992

(Continued)

OTHER PUBLICATIONS

Web page, "Heart Valve Prostheses: Ball Valves", at URL=http://www.csmc.edu/cvs/md/valve/ballvlvs.htm, p. 3 of 4, (printed Aug. 2, 2002).

*Primary Examiner*—David H. Willse
*Assistant Examiner*—Javier G. Blanco
(74) *Attorney, Agent, or Firm*—Townsend & Townsend & Crew LLP; Mark D. Barrish

(57) ABSTRACT

The present invention provides improved devices and methods for replacing or repairing a malfunctioning heart valve. In particular, improved minimally invasive methods and devices are provided for percutaneous transcatheter implantation of expansible prosthetic heart valves within or adjacent a valved anatomic site within the heart. In one embodiment, an expansible prosthetic heart valve comprises an implantable structure, a flexible membrane, and a membrane support. The implantable structure is expansible from a first reduced diameter to a second enlarged diameter and has a flow path therethrough. The flexible membrane is positionable in the flow path for permitting flow in a first direction and substantially resisting flow in a second direction. The membrane support is positionable in the flow path and affixed to the implantable structure.

27 Claims, 6 Drawing Sheets

U.S. PATENT DOCUMENTS

| | | | |
|---|---|---|---|
| 6,440,164 B1 * | 8/2002 | DiMatteo et al. | 623/1.24 |
| 6,454,799 B1 | 9/2002 | Schreck | |
| 6,458,153 B1 * | 10/2002 | Bailey et al. | 623/1.24 |
| 6,482,228 B1 | 11/2002 | Norred | |
| 6,503,272 B2 * | 1/2003 | Duerig et al. | 623/1.24 |
| 6,669,724 B2 * | 12/2003 | Park et al. | 623/1.24 |
| 2001/0007956 A1 | 7/2001 | Letac et al. | |
| 2001/0021872 A1 | 9/2001 | Bailey et al. | |
| 2002/0032481 A1 * | 3/2002 | Gabbay | 623/2.11 |
| 2002/0058995 A1 | 5/2002 | Stevens | |
| 2002/0116024 A1 * | 8/2002 | Goldberg et al. | 606/200 |
| 2002/0138135 A1 * | 9/2002 | Duerig et al. | 623/1.24 |
| 2003/0181974 A1 * | 9/2003 | Xie et al. | 623/1.24 |
| 2004/0193253 A1 * | 9/2004 | Thorpe et al. | 623/1.24 |
| 2004/0225354 A1 * | 11/2004 | Allen et al. | 623/2.11 |
| 2005/0228495 A1 * | 10/2005 | Macoviak | 623/2.18 |

FOREIGN PATENT DOCUMENTS

WO     WO 200205888 A1 *   1/2002

* cited by examiner

PERCUTANEOUS TRANSCATHETER HEART VALVE REPLACEMENT

BACKGROUND OF THE INVENTION

1. Field of the Invention

The present invention relates generally to medical devices and methods. More particularly, the present invention provides minimally invasive methods and devices for percutaneous transcatheter implantation of expansible prosthetic heart valves within or adjacent a valved anatomic site within the heart.

Natural heart valves, such as aortic valves, mitral valves, pulmonary valves, and tricuspid valves, often become damaged by disease in such a manner that they fail to maintain bodily fluid flow in a single direction. A malfunctioning heart valve may be stenotic (i.e., heart leaflets are closed down) or regurgitant (i.e., heart leaflets are wide open). Maintenance of blood flow in a single direction through the heart valve is important for proper flow, pressure, and perfusion of blood through the body. Hence, a heart valve that does not function properly may noticeably impair the function of the heart.

The etiologies commonly associated with a malfunctioning heart valve may be congenital, acquired, infectious, or degenerative. The most commonly affected heart valves are the aortic and mitral valves. It is believed that rheumatic heart disease, trauma, and bacterial endocarditis may be largely responsible for aortic stenosis and regurgitation. Common causes of mitral valve malfunctioning may be rheumatic diseases, enlargement of a left ventricle, or endocarditis. Pulmonary valve stenosis may be a congenital heart defect. Common causes of tricuspid valve malfunctioning may be rheumatic heart disease or heart defect.

Cardiac valve prostheses are well known in the treatment of heart disease to replace malfunctioning heart valves. Heart valve replacement generally has been accomplished by major open heart surgery. This is a serious operation that requires general anesthesia, full cardiopulmonary bypass with complete cessation of cardiopulmonary activity, an extended hospitalization stay, and several more weeks to months of recuperation time. For some patients, open heart surgery is not an option because of the critical condition of the patient, advanced age, co-existing infection, or other physical limitations.

An alternative treatment regiment to open heart surgery is minimally invasive intravascular delivery and implantation of prosthetic heart valves, typically by way of catheterization. In minimally invasive procedures, a catheter is used to insert a mechanical or bioprosthetic valve in a lumen of a central blood vessel via percutaneous entry through a distal blood vessel. Typically, such percutaneous prosthetic valve devices comprise an expandable stent segment, a stent anchoring segment, and a flow-regulation segment, such as a ball valve or a leaflet. While such minimally invasive prosthetic devices and methods are promising from safety, patient recovery, and cost standpoints, some drawbacks still need to be addressed. For example, some prosthetic heart valve structures which attempt to mimic locally stiffened tissue of natural valves often fatigue or may even fail with continued or prolonged opening and closing of the valve. This may especially be a problem for prosthetic aortic valve replacements due to the associated high blood pressures and flow rates at this anatomic site.

For these reasons, it would be desirable to provide improved devices and methods for replacing or repairing a malfunctioning heart valve. In particular, it would be desirable to provide improved minimally invasive methods and devices for percutaneous transcatheter implantation of expansible prosthetic heart valves within or adjacent a valved anatomic site within the heart. In particular, it would be desirable to provide improved prosthetic heart valve devices that reduce or inhibit fatigue and/or failure of the valve, particularly the flow-regulation mechanism, during continued or prolonged opening and closing of the valve. It would be further desirable to provide improved prosthetic heart valve devices that effectively maintain bodily fluid flow in a single direction and open and close with pressure and/or flow change of blood through the body. At least some of these objectives will be met by the devices and methods of the present invention described hereinafter.

2. Description of the Background Art

Percutaneous aortic valve replacements are described in U.S. Pat. Nos. 6,482,228 and 5,855,601 and U.S. Publication Nos. 2002/0058995 and 2001/0007956. Other artificial heart valves for implantation within a blood vessel are described in U.S. Pat. Nos. 6,454,799; 6,296,662; 5,957,949; 5,413,599; 4,994,077; 4,352,211; and 3,671,979. Percutaneous venous valve replacements are described in U.S. Pat. No. 6,299,637 and U.S. Publication Nos. 2002/0138135 and 2001/0021872.

The full disclosures of each of the above references are incorporated herein by reference.

BRIEF SUMMARY OF THE INVENTION

The present invention provides improved devices and methods for replacing or repairing a malfunctioning heart valve. In particular, improved minimally invasive methods and devices are provided for percutaneous transcatheter implantation of expansible prosthetic heart valves within or adjacent a valved anatomic site within the heart. In particular, the improved prosthetic heart valve devices of the present invention reduce or inhibit fatigue and/or failure of the valve, particularly the flow-regulation mechanism, during continued or prolonged opening and closing of the valve. Such improved prosthetic heart valve devices also efficiently maintain bodily fluid flow in a single direction and open and close with pressure and/or flow change of blood through the body.

In a first aspect of the present invention, an expansible prosthetic heart valve comprises an implantable structure, a flexible membrane, and a membrane support. The implantable structure is expansible from a first reduced diameter to a second enlarged diameter and has a flow path therethrough. The flexible membrane is positionable in the flow path for permitting flow in a first direction and substantially resisting flow in a second direction. The membrane support is positionable in the flow path and affixed to the implantable structure.

The membrane support is disposed in the flow path when the implantable structure has the second enlarged diameter. The membrane support comprises at least one radial rib, typically a plurality of radial ribs, extending across the blood flow path of a valve annulas. Preferably, the membrane support comprises a circular or cap-like wire frame extending across an axis of the implantable structure. The membrane support may comprise a separate structure or in the alternative may be integrally formed with the implantable structure so as to define an integral framework. Advantageously, the membrane support reduces and/or inhibits movement of the flexible membrane in the second direction when the prosthetic heart valve is closed. Further, the membrane support need not flex or contract significantly during opening and closing of the flow path with the flexible membrane. As such, fatigue and/or failure of the prosthetic valve, particularly the membrane support and flexible membrane, may be significantly reduced and/or inhibited during continued or prolonged opening and closing of the valve.

The flexible membrane is disposed in the flow path when the implantable structure has the second enlarged diameter. The flexible membrane functions as a one-way valve member to efficiently maintain bodily fluid flow in a single direction. The flexible membrane opens and closes with pressure and/or flow change of blood through the body so as to allow the blood to flow in the first direction (i.e., prosthetic heart valve is open) and to inhibit the flow of blood in the second or opposite direction (i.e., prosthetic heart valve is closed). The flexible membrane is preferably affixed to a central portion of the membrane support. However, it will be appreciated that the flexible membrane may be optionally attached anywhere along the circular wire frame of the membrane support or be attached to the implantable structure. In operation, the flexible membrane opens and closes somewhat like an umbrella. Typically, the flexible membrane has a substantially circular shape when the prosthetic heart valve is closed and a substantially conical shape when the prosthetic heart valve is open. In some instances, the flexible membrane may comprise at least one leaflet, typically two to three leaflets, or the flexible membrane may comprise a displaceable, expandable valve member. The flexible membrane may be formed form a variety of materials but will typically comprise an expanded polytetrafluoroethylene or biological materials.

The implantable structure generally comprises a stent-like tubular framework which primarily anchors the prosthetic heart valve within or adjacent the defective valve annulus of the heart. The implantable structure in some instances may also maintain luminal patency, particularly when the defective valve is stenotic. The implantable structure and the membrane support will typically comprise resiliently expanding shape memory alloy or like materials, but may be plastically expandable in some embodiments. In this embodiment, the implantable structure and the membrane support are fixed relative to one another and do not substantially flex every time the flow path is opened or closed by the flexible membrane. The tubular framework preferably comprises a plurality of struts, wherein at least three struts are longer than the remaining struts. The three elongate struts are of benefit in providing optimal orientation of the prosthetic heart valve during implantation. The tubular framework may further comprise a plurality of radial protrusions, such as hooks or anchoring barbs, extending beyond the framework when the framework is implanted within or adjacent an intraluminal site. Such radial protrusions that extend circumferentially and longitudinally from an outer surface of the tubular framework further aid in anchoring the prosthetic heart valve.

In some instances, the implantable structure or membrane support may be covered with a layer of expanded polytetrafluoroethylene or biological materials. Further, at least a portion of the implantable structure, flexible membrane, or membrane support may be coated with an anit-thrombogenic substance, such as anti-coagulants, to minimize or prevent any clot formations. All three components of the prosthetic heart valve are expandable from a first reduced profile configuration for endoluminal valve insertion and advancement thorough the vasculature to a second enlarged profile configuration for operation as a valve.

In a second aspect of the present invention, an expansible prosthetic heart valve comprises an implantable structure, a displaceable, expandable valve member, and a valve member support. The implantable structure is expansible from a first reduced diameter to a second enlarged diameter and has a flow path therethrough. The displaceable, expandable valve member is positionable in the flow path for permitting flow in a first direction and substantially resisting flow in a second direction. The valve member support is positionable in the flow path at least when the prosthetic heart valve is closed. The valve member and valve member support are disposed in the flow path when the implantable structure has the second enlarged diameter.

The displaceable or moveable valve member in this embodiment is preferably affixed to the valve member support. Beneficially, the valve member support acts to support the valve member while the valve member inhibits the flow of blood in the second direction when the prosthetic heart valve is closed. The displaceable valve member and valve member support may together comprise an expandable ball valve. The ball valve may be coupled to the implantable structure at a hinge point, wherein the ball valve is centrally supported. Alternatively, the ball valve may be axially slidable or moveable relative to the implantable structure. Irrespective, the valve member and valve member support are displaced during opening and closing of the flow path.

In a third aspect of the present invention, an expansible prosthetic heart valve comprises a tubular framework, a flexible membrane, and a membrane support. The tubular framework is expansible from a first reduced diameter to a second enlarged diameter and has a flow path along a tubular axis. The framework in this embodiment preferably comprises a plurality of struts, wherein at least three of the struts are longer than the remaining struts. The flexible membrane is positionable in the flow path for permitting flow in a first direction and substantially resisting flow in a second direction. The membrane support is affixed to the tubular framework and disposed in the flow path when the framework has the second enlarged diameter. In particular, the membrane support inhibits movement of the flexible membrane in the second direction when the prosthetic heart valve is closed and does not substantially flex or contract during opening and closing of the flow path with the flexible membrane.

In a fourth aspect of the present invention, methods for implanting an expansible heart valve are provided. One method comprises providing a prosthetic heart valve having an expansible structure, a flexible membrane, and a membrane support. The expansible structure is implanted within or adjacent an intraluminal site. The structure is expanded from a first reduced diameter to a second enlarged diameter, wherein a flow path extends therethrough. The flexible membrane is positioned in the flow path for permitting flow in a first direction and substantially resisting flow in a second direction. The membrane support is disposed in the flow path when the framework has the second enlarged diameter. In particular, the membrane support does not flex during opening and closing of the flow path by the flexible membrane.

The intraluminal site may comprise an aortic valve to facilitate blood flow from a left ventricle to an aorta, a mitral valve to facilitated blood flow from a left atrium to the left ventricle, a pulmonary valve to facilitate blood flow from a right ventricle to pulmonary arteries, or a tricuspid valve to facilitate blood flow from a right atrium to the right ventricle. As discussed above, the membrane support is preferably affixed to the structure, wherein the membrane support and structure are fixed during opening and closing of the flow path by the flexible membrane. Alternatively, the flexible membrane may comprise an expandable valve member affixed to the membrane support. In such an embodiment, the expandable valve member and membrane support are displaced at a hinge or in an axial direction relative to the structure.

A further understanding of the nature and advantages of the present invention will become apparent by reference to the remaining portions of the specification and drawings.

DETAILED DESCRIPTION OF THE INVENTION

The present invention provides improved devices and methods for replacing or repairing a malfunctioning heart valve. In particular, improved minimally invasive methods and devices are provided for percutaneous transcatheter implantation of expansible prosthetic heart valves within or adjacent a valved anatomic site within the heart. The expansible prosthetic heart valve may be implanted by catheterization techniques so as to take advantage of the collapsible and self expanding characteristics of the heart valve of the present invention.

Figure 1A:
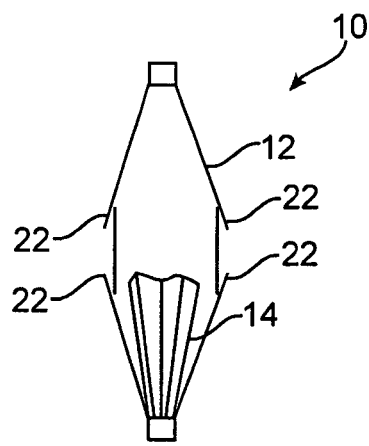
FIGS. 1A–1D illustrate an exemplary embodiment of an expansible prosthetic heart valve constructed in accordance with the principles of the present invention.
Figure 1B:
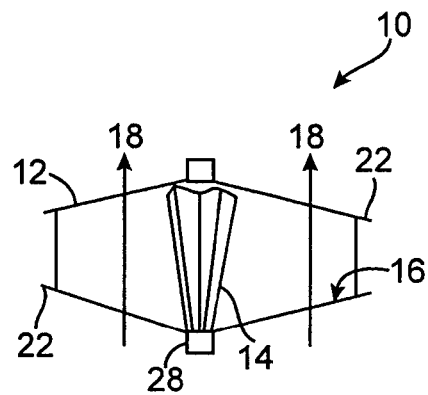
Figure 1C:
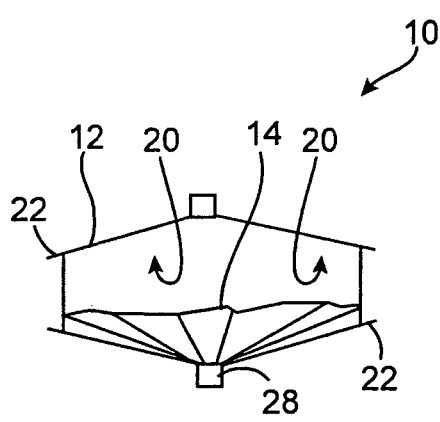
Figure 1D:
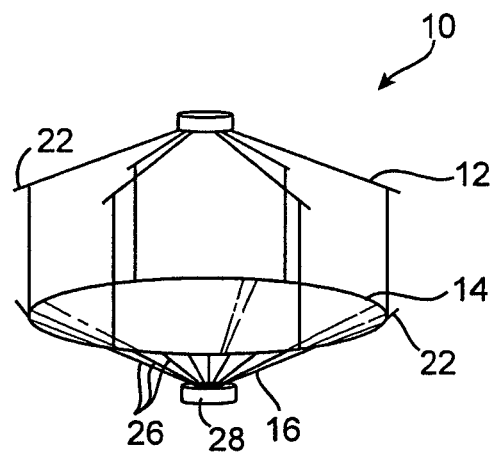

FIGS. 1A–1D illustrate an exemplary embodiment of an expansible prosthetic heart valve constructed in accordance with the principles of the present invention. The expansible prosthetic heart valve 10 comprises an implantable structure 12, a flexible membrane 14, and a membrane support 16. The implantable structure 12 is expansible from a first reduced diameter, as shown in FIG. 1A, to a second enlarged diameter, as shown in FIGS. 1B–1D, and has a flow path along a structure axis. The flexible membrane 14 is positionable in the flow path for permitting flow in a first direction, as illustrated by arrow 18 in FIG. 1B, and substantially resisting flow in a second direction, as illustrated by arrow 20 in FIG. 1C. The membrane support 16 is positionable in the flow path and affixed to the implantable structure 12, as shown in FIGS. 1B and 1D. It will be appreciated that the following depictions are for illustration purposes only and do not necessarily reflect the actual shape, size, or dimensions of the expansible prosthetic heart valve 10. This applies to all depictions hereinafter.

The implantable structure 12 generally comprises a tubular framework, Such as a stent, which primarily anchors the prosthetic heart valve 10 within or adjacent the defective valve annulus of the heart. The implantable structure 12 provides stability and prevents the prosthetic heart valve 10 from migrating or embolizing after it has been implanted. The tubular framework 12 may further comprise a plurality of radial protrusions 22, such as hooks or anchoring barbs, extending beyond the framework 12 when the framework is implanted within or adjacent an intraluminal site. Such radial protrusions 12 that extend circumferentially and/or longitudinally from an outer surface of the tubular framework 12 further aid in anchoring the prosthetic heart valve 10 within or adjacent the defective valve annulus of the heart.

The implantable structure 12 may be self expanding and is suitable for placement within or adjacent a valved intraluminal site. The valved intraluminal site preferably comprises an aortic valve, mitral valve, pulmonary valve, or tricuspid valve annulus of the heart. It will be appreciated however that the present invention may also find use in valved intraluminal sites other than in the heart. For example, the present invention may be applied to venous valves as well. Self expanding structures 12 are provided by utilizing resilient metals, such as a superelastic shape memory alloy, e.g., NITINOL™ alloys, tempered stainless steel, spring stainless steels, or the like, and forming the tubular framework so that it possesses its desired, radially expanded diameter when it is unconstrained, i.e., released from radially constraining forces of a sheath. In order to remain anchored in the intraluminal site, the implantable structure 12 will remain partially constrained by the intraluminal site. The self-expanding implantable structure 12 may be tracked and delivered in its radially constrained configuration, e.g., by placing the implantable structure 12 within a delivery sheath or tube and removing the sheath at the valved site. It will be appreciated however that the implantable structure may in some instances be plastically expandable.

The dimensions of the implantable structure 12 will depend on its intended use. Typically, the implantable structure 12 will have a length in a range from about 10 mm to about 60 mm for heart valve applications. The first reduced (radially collapsed) diameter of the implantable structure 12 will usually be in a range from about 2 mm to about 8 mm. The second enlarged (radially expanded) diameter of the implantable structure 12 will usually be in a range from about 10 mm to about 60 mm. The implantable structure may be fabricated using standard stent fabrication techniques.

Figure 1E:
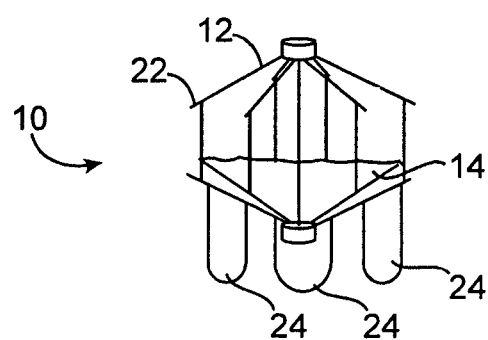
FIG. 1E illustrates the expansible prosthetic heart valve of FIGS. 1A–1D wherein an anchoring framework includes three elongate struts.

Referring now to FIG. 1E, an alternative embodiment of the anchoring framework 12 is illustrated. In particular, the tubular framework comprising a plurality of struts includes at least three struts 24 that are longer than the remaining struts. The three elongate struts 24 are of benefit in providing self orientation of the prosthetic heart valve 10 during implantation. For example, the elongate struts 24 may be easily positioned at the roots of a defective aortic valve annulus so that the heart valve is positioned in the original location of the natural valve. Such self orientation in this case is important because it ensures that openings in left and right coronary arteries are not blocked during and/or after valve 10 operation.

Referring back to FIGS. 1B and 1D, the membrane support 16 is disposed in the flow path when the implantable structure 12 has been expanded. In particular, the membrane support 16 is expandable from a first reduced profile configuration for endoluminal valve insertion and advancement thorough the vasculature (FIG. 1A) to a second enlarged profile configuration for operation as a valve (FIGS. 1B–1D). The membrane support 16 typically comprises a plurality of radial ribs 26 extending across the blood flow path of the valve annulas. Preferably, the membrane support 16 comprises a circular or cap-like wire frame extending across an axis of the implantable structure. The membrane support 16 may have a structure similar to that of and be optionally integrally formed with the implantable structure 12 so as to define an integral framework. The membrane support 16 generally comprises resilient metals, such as a superelastic shape memory alloy, e.g., NITINOL™ alloys, tempered stainless steel, spring stainless steels, or the like. Advantageously, the membrane support 16 reduces and/or inhibits movement of the flexible membrane 14 in the second direction 20 when the prosthetic heart valve is closed. Further, as illustrated in this embodiment, the implantable structure 12 and the membrane support 16 are fixed relative to one another and as such do not substantially flex every time the flow path is opened (FIG. 1B) or closed (FIGS. 1C and 1D) by the flexible membrane 14. Hence, fatigue and/or failure of the prosthetic valve 10, particularly the membrane support 16 and flexible membrane 14, may be significantly reduced and/or inhibited during continued or prolonged opening and closing of the valve 10.

The flexible membrane 14 is disposed in the flow path when the implantable structure 12 has the second enlarged diameter. The flexible membrane 14 is expandable from a first reduced profile configuration (FIGS. 1A and 1B) to a second enlarged profile configuration (FIGS. 1C and 1D). The flexible membrane 14 functions as a one-way valve member to efficiently maintain bodily fluid flow in a single direction, as depicted by arrow 18. The flexible membrane 14 opens and closes with pressure and/or flow change of blood through the body so as to allow the blood to flow in the first direction 18 when the prosthetic heart valve 10 is open and to substantially inhibit the flow of blood in the second or opposite direction 20 when the prosthetic heart valve 10 is closed. The flexible membrane 14 is preferably affixed to a central portion 28 of the membrane support 16. It will be appreciated that the flexible membrane may alternatively be attached anywhere along the circular wire frame of the membrane support 16 or be attached to the implantable structure 12. Further, the flexible membrane 14 may be disposed within or outside (not shown) an interior of the implantable structure 12. In operation, the flexible membrane 14 opens and closes somewhat like an umbrella. Typically, the flexible membrane 14 has a substantially circular shape when the prosthetic heart valve 10 is closed (FIG. 1D) and a substantially conical shape when the prosthetic heart valve 10 is open (FIG. 1B).

The flexible membrane 14 may be formed form a variety of materials including expanded polytetrafluoroethylene or biological materials. Expanded polytetrafluoroethylene may comprise expanded TEFLON™ polymers, high density polyethylene, polyurethane, a combination thereof, or like polymers. Biological materials include homograft (a recent human harvest), allograft (a stored human harvest), or xenograft (a stored animal harvest). Homografts and allografts are rare because of problems of locating and matching human donors in both tissue type and size. Xenografts are common and well accepted, usually from bovine, ovine, swine, or porcine pericardium, or a combination thereof. In some instances, a periphery of the implantable structure 12 may be covered with a layer of expanded polytetrafluoroethylene or biological materials. An expanded polytetrafluoroethylene or biological tissue covering may promote healing and/or endothelialization as well as provide additional anchoring support for the heart valve. Furthermore, such a covering may aid in incorporation of the implantable structure 12 within the local tissue (i.e., an endothelial surface may cover the implantable structure 12). Further, at least a portion of the implantable structure 12, flexible membrane 14, or membrane support 16 may be coated with an anit-thrombogenic substance, such as anticoagulants, to minimize or prevent any clot formations.

Figure 2A:
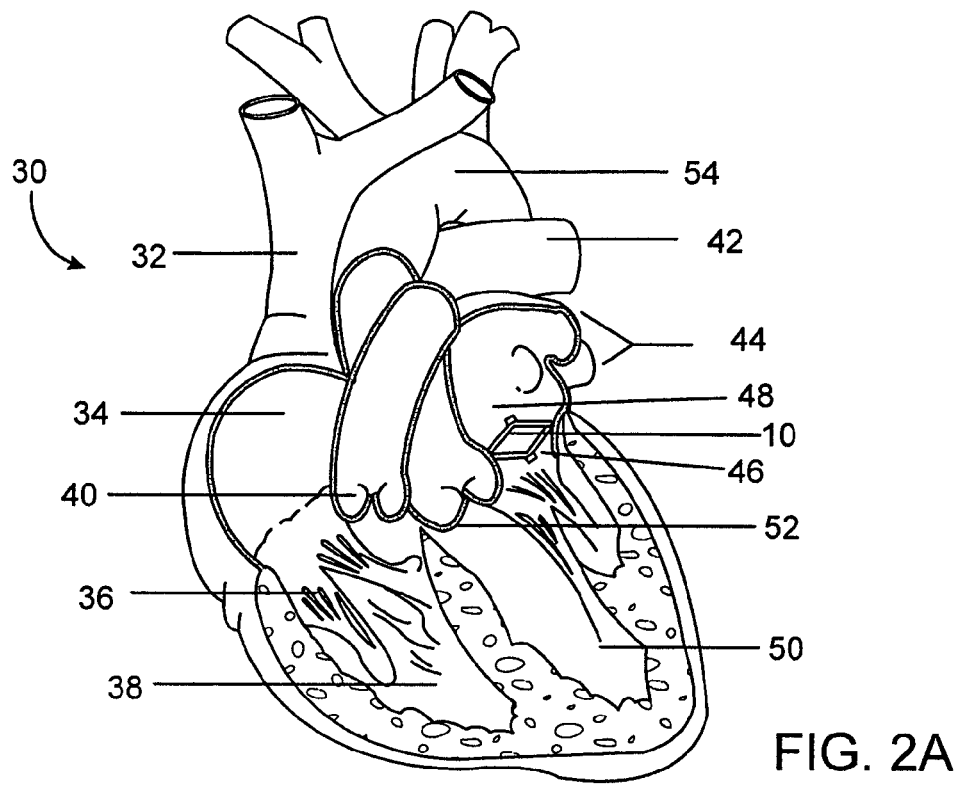
FIGS. 2A and 2B illustrate cross sectional views of a human heart with the expansible prosthetic heart valve of FIGS. 1A–1D implanted within or adjacent a mitral valve and aortic valve respectively.
Figure 2B:
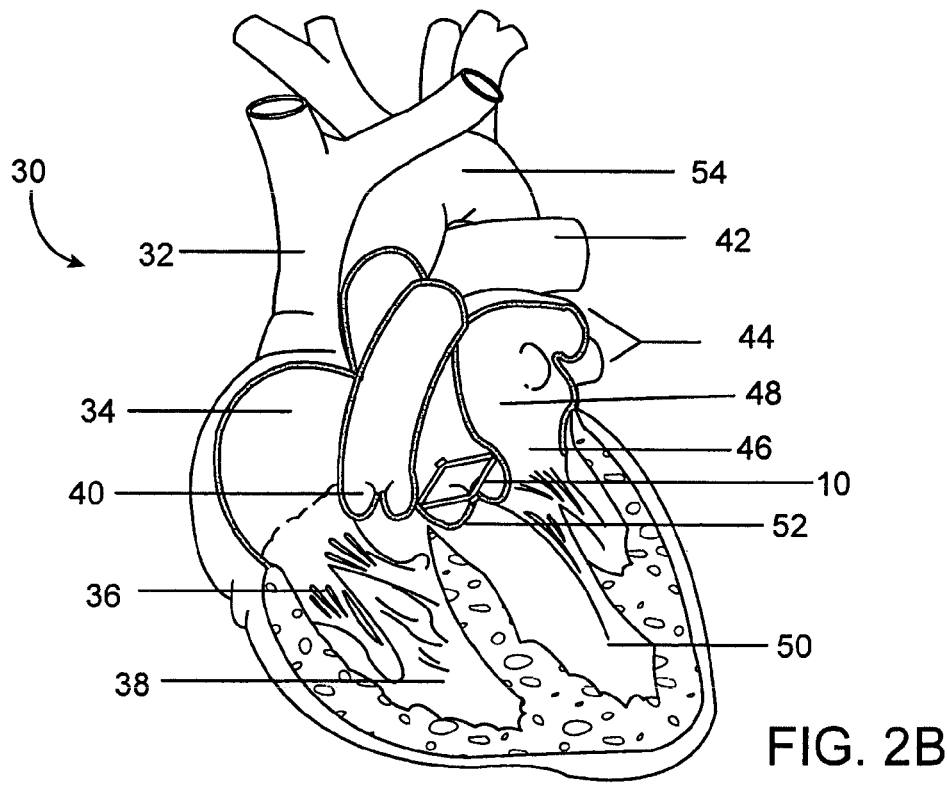

FIGS. 2A and 2B illustrate cross sectional views of a human heart with the expansible prosthetic heart valve 10 implanted within or adjacent a mitral valve and aortic valve respectively. The natural flow path of blood through the heart 30 starts from superior and inferior vena cavas 32 to a right atrium 34 and through a tricuspid valve 36 to facilitate blood flow from the right atrium 34 to a right ventricle 38. A pulmonary valve 40 facilitates blood flow from the right ventricle 38 to the pulmonary arteries 42. The blood is then oxygenated by the lungs and returned back to the heart via pulmonary veins 44. A mitral valve 46 then facilitates blood flow from a left atrium 48 to a left ventricle 50, as shown by the implanted heart valve 10 in FIG. 2A. An aortic valve 52 facilitates blood flow from the left ventricle 50 to an aorta 54 for perfusion of oxygenated blood through the peripheral body, as shown by the implanted heart valve 10 in FIG. 2B.

Figure 3A:
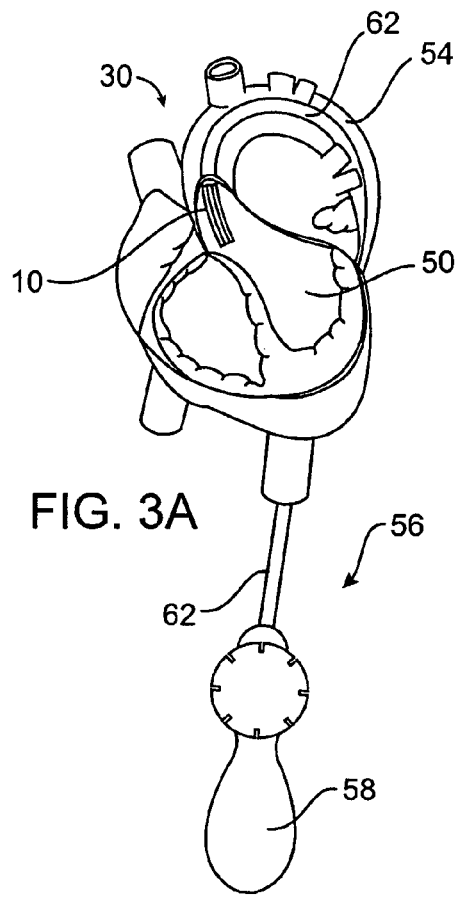
FIGS. 3A–3C illustrate a method for implanting the expansible prosthetic heart valve of FIGS. 1A–1D within or adjacent an intraluminal site.
Figure 3B:
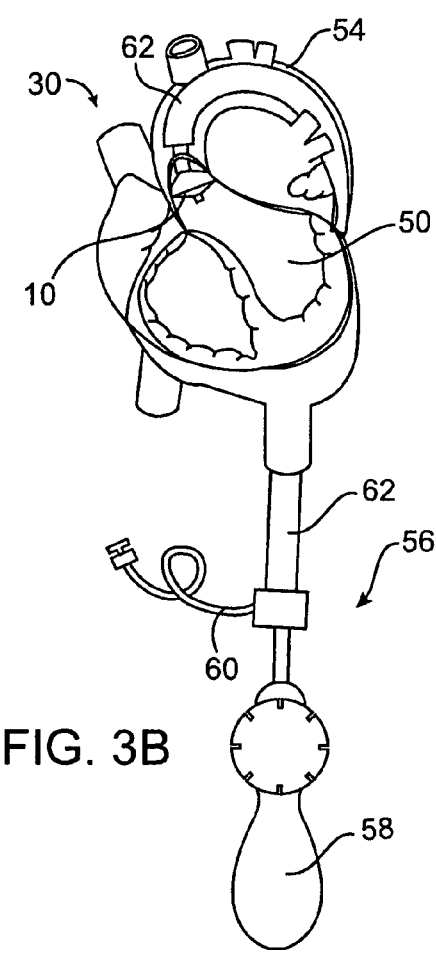
Figure 3C:
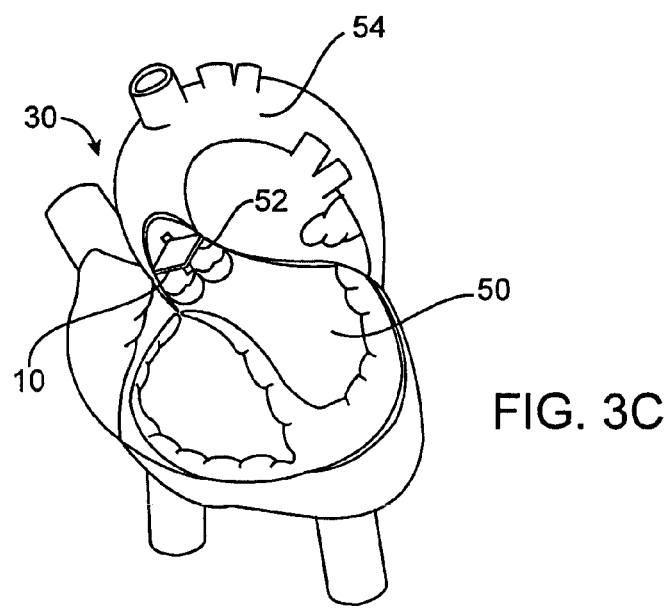

FIGS. 3A–3C illustrate a method for implanting the expansible prosthetic heart valve 10 within or adjacent an aortic intraluminal site 52. The method comprises providing a prosthetic heart valve 10 having an expansible structure 12, a flexible membrane 14, and a membrane support 16. The expansible structure 10 is implanted by percutaneously passing a valve delivery system 56 endoluminally through an anatomic passageway to the valved anatomic site 52 within the heart 30. The anatomic passageway for introduction of the delivery system 56 into the vasculature may comprise a distal blood vessel, such as femoral or brachial arteries or veins. It will be appreciated that the particular anatomic passageway for entry is dependent upon the particular location of the malfunctioning heart valve to be replaced or repaired. For example, an aortic valve replacement 52 may be achieved through access from the femoral or brachial arteries and through the arch of the aorta 54. Still further, a mitral valve replacement 46 may be achieved through access from the venous system, including the inferior and/or superior vena cava 32, and a transseptal puncture of an atrial septum from the right atrium 34 to the left atrium 48. The valve delivery system 56 includes a control handle 58, injection port 60, and a valve access sheath 62.

As shown in FIG. 3A, the prosthetic heart valve 10 is collapsed inside the delivery system 56. The self expanding implantable structure 12 may be delivered in its radially constrained configuration, e.g., by placing the implantable structure within the delivery sheath 62 and proximally removing the sheath 62 at the valved site. Once the valve 10 is positioned in an optimal location, it may be exposed via sheath removal 62 and expanded from a first reduced diameter (FIG. 3A) to a second enlarged diameter (FIG. 3B), wherein a flow path extends therethrough. As discussed above, implantation of the valve 10 may further comprise aligning the implantable structure 12 within the aortic site 52 with the three elongate struts 24 to effect self orientation of the valve. In order to remain anchored in the intraluminal site 52, the implantable structure 12 will remain partially constrained by the intraluminal site. Moreover, a plurality of hooks or radial protrusions 22 may further stabilize the implantable structure 12 within the aortic site 52.

As shown in FIG. 3C, the prosthetic heart valve 10 is shown detached from the delivery system 56 and in its expanded state. The flexible membrane 14 is positioned in the flow path for permitting flow in a first direction and substantially resisting flow in a second direction. In this depiction, the valve 10 is shown closed so as to prevent any regurgitation or back flow from the aorta 54. The membrane support 16 is also positioned in the flow path. In particular, the membrane support 16 does not flex during opening and closing of the flow path by the flexible membrane 14. All three components of the prosthetic heart valve 10 are expandable from a first reduced profile configuration for endoluminal valve delivery thorough the vasculature, as shown in FIG. 3A, to a second enlarged profile configuration for operation as a valve, as shown in FIGS. 3B and 3C. It will be appreciated that all three components of the heart valve 10 may also be reduced from the second enlarged profile configuration for subsequent repositioning or retrieval of the valve 10. The location and the function of the prosthetic heart valve 10 may be tracked by injecting contrast media inside the chambers of the heart 30 and viewing the flow pattern under fluoroscopy.

Figure 4A:
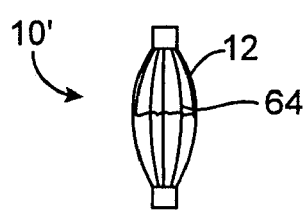
FIGS. 4A–4D illustrate a second embodiment of the expansible prosthetic heart valve constructed in accordance with the principles of the present invention.
Figure 4B:
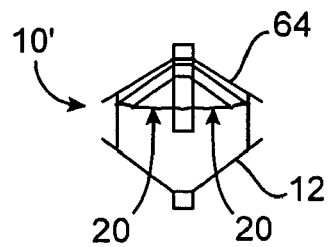
Figure 4C:
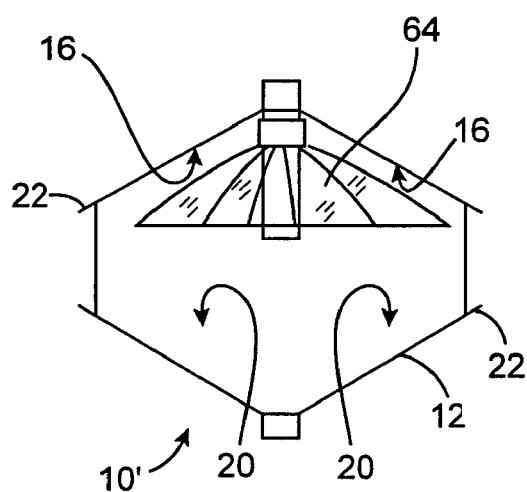
Figure 4D:
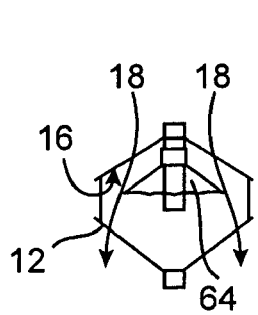

Referring now to FIGS. 4A–4D, a second embodiment of the expansible prosthetic heart valve 10' constructed in accordance with the principles of the present invention is illustrated. The prosthetic heart valve 10' remains the same as described above with the exception of the flexible membrane structure. In this embodiment, the flexible membrane comprises a displaceable, expandable valve member 64. FIG. 4A illustrates all three components of the valve 10' in a first collapsed state for intraluminal delivery. FIGS. 4B and 4C illustrate all three components of the valve 10' in an expanded state, wherein the prosthetic heart valve 10' is in a closed configuration so as to substantially resist flow in a second direction 20. FIG. 4D also illustrates all three components of the valve 10' in an expanded state. In FIG. 4D, however, the expanded flexible membrane 64 is shown axially displaced relative to the implantable structure 12 and the membrane support 16 so that the valve 10' is in an open configuration so as to permit flow in a first direction 18.

Figure 5A:
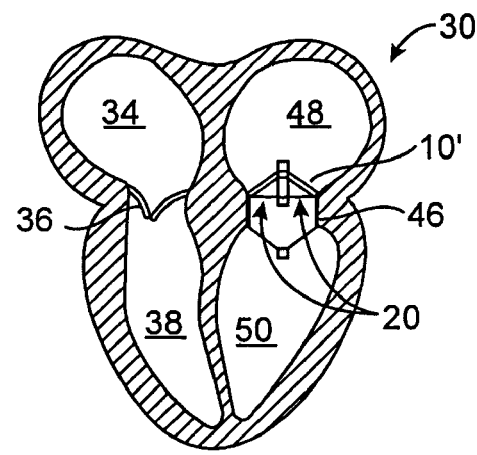
FIGS. 5A and 5B illustrate cross section views of a human heart with the expansible prosthetic heart valve of FIGS. 4A–4D implanted within or adjacent a mitral valve.
Figure 5B:
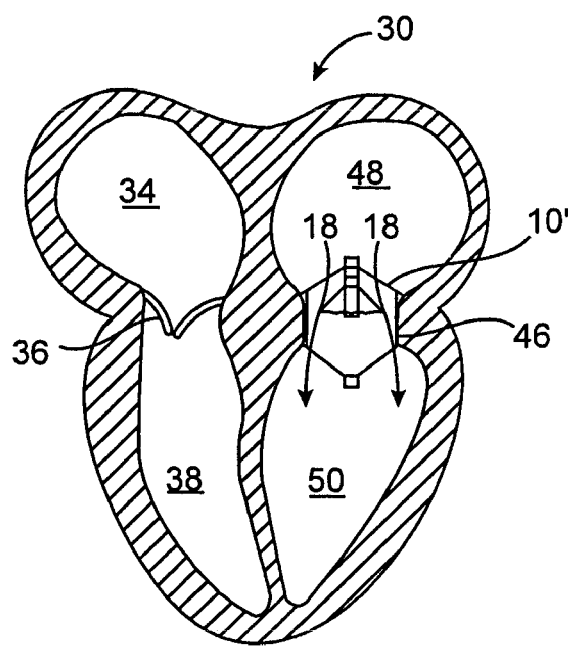

FIGS. 5A and 5B illustrate cross section views of the human heart 30 with the expansible prosthetic heart valve 10' implanted within or adjacent a mitral valve 46. FIG. 5A illustrates the expanded prosthetic heart valve 10' in a closed configuration so as to substantially resist flow in a second direction 20. FIG. 5B illustrates the expanded valve 10' in an open configuration so as to permit flow in a first direction 18 from the left atrium 48 through the left ventricle 50.

Figure 6A:
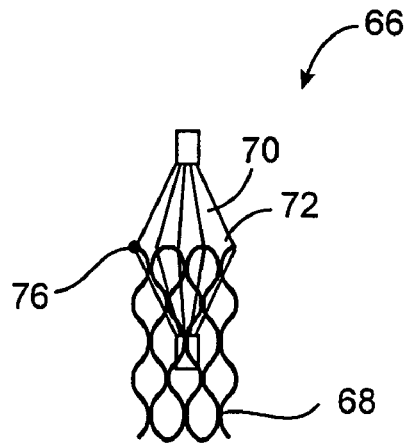
FIGS. 6A–6D illustrate a third embodiment of the expansible prosthetic heart valve constructed in accordance with the principles of the present invention.
Figure 6B:
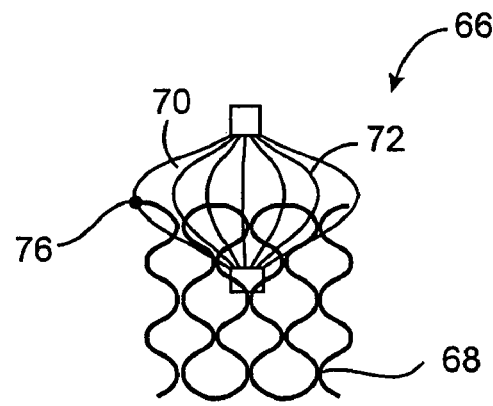
Figure 6C:
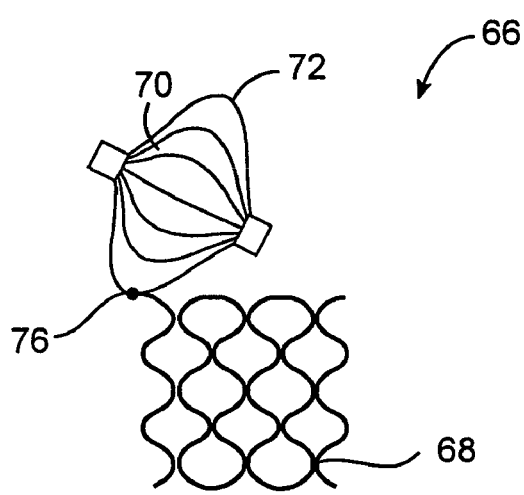
Figure 6D:
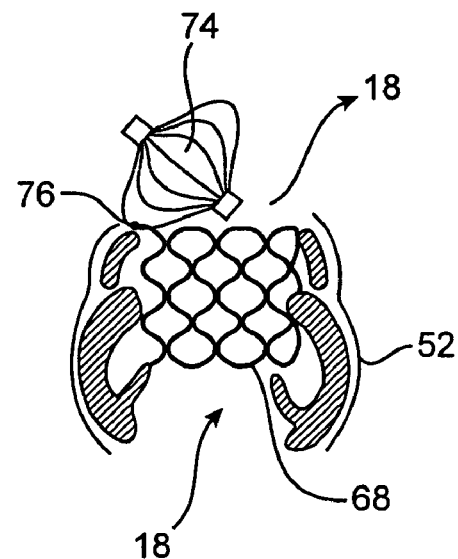

Referring now to FIGS. 6A–6D, a third embodiment of the expansible prosthetic heart valve 66 constructed in accordance with the principles of the present invention is illustrated. In this embodiment, an expansible prosthetic heart valve 66 comprises an implantable structure 68, a displaceable, expandable valve member 70, and a valve member support 72. The implantable structure 68 is expansible from a first reduced diameter, as shown in FIG. 6A, to a second enlarged diameter, as shown in FIGS. 6B–6D, and has a flow path therethrough. The displaceable, expandable valve member 70 is positionable in the flow path for permitting flow in a first direction 18 (FIGS. 6C and 6D) and substantially resisting flow in a second direction (FIG. 6B). The valve member support 72 is positionable in the flow path at least when the prosthetic heart valve 66 is closed. The valve member 70 and valve member support 72 are disposed in the flow path when the implantable structure 68 has the second enlarged diameter.

The displaceable or moveable valve member 70 in this embodiment is preferably affixed to the valve member support 72. Beneficially, the valve member support 72 acts to support the valve member 70 while the valve member 70 inhibits the flow of blood in the second direction when the prosthetic heart valve is closed, as shown in FIG. 6B. The displaceable valve member 70 and valve member support 72 may together comprise an expandable ball valve 74. The valve member support 72 and the implantable structure 68 preferably comprise a framework of resilient metals, such as a superelastic shape memory alloy, e.g., NITINOL™ alloys, tempered stainless steel, spring stainless steels, or the like. The flexible membrane may comprise expanded polytetrafluoroethylene such as expanded TEFLON™ polymers, high density polyethylene, polyurethane, a combination thereof, or like polymers, which covers the valve member support 72.

In this embodiment, the ball valve 74 may be coupled to the implantable structure 68 at a hinge point 76, wherein the ball valve 74 is centrally supported. FIG. 6C illustrates displacement of the ball valve 74 at the hinge 76 relative to the implantable structure 68 so that the valve 66 is in an open configuration. FIG. 6D illustrates the expanded valve 66 in an open configuration in the aortic valve 52 of the heart 30 so as to permit flow in a first direction 18 from the left ventricle 50 through the aorta 54.

Figure 7A:
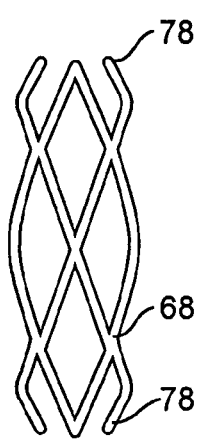
FIGS. 7A–7F illustrate a fourth embodiment of the expansible prosthetic heart valve constructed in accordance with the principles of the present invention.
Figure 7B:
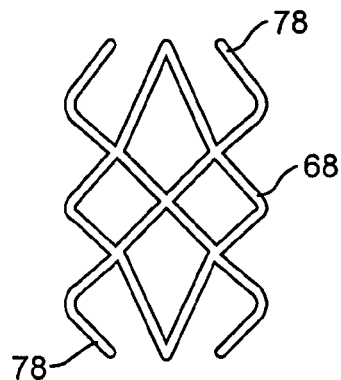
Figure 7C:
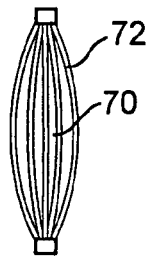
Figure 7D:
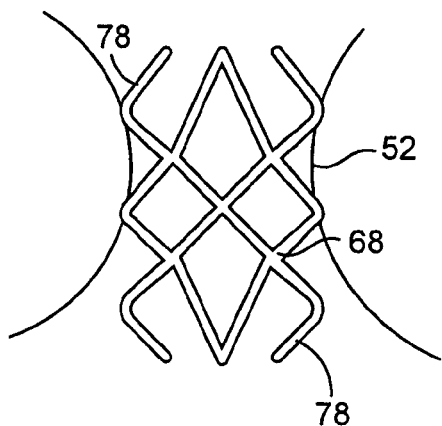
Figure 7E:
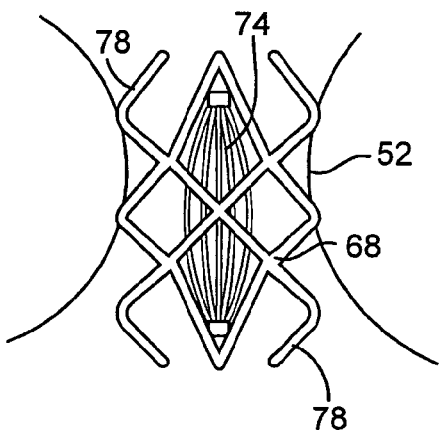
Figure 7F:
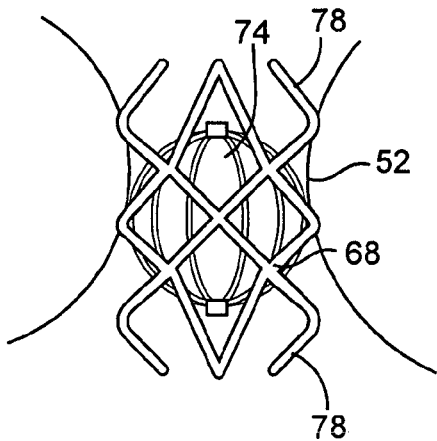

Referring now to FIGS. 7A–7F, a fourth embodiment of the expansible prosthetic heart valve constructed in accordance with the principles of the present invention is illustrated. The prosthetic heart valve remains the same as described above with the exception of how the ball valve 74 is displaced. Specifically, as shown in FIGS. 7A–7F, the ball valve 74 may be axially slidable or moveable relative to the implantable structure 68. The implantable structure 68 is illustrated in a first reduced diameter, as shown in FIG. 7A, and a second enlarged diameter, as shown in FIGS. 7B and 7D–7F. FIGS. 7C and 7E illustrate the ball valve 74 in a first collapsed configuration and in a second expanded configuration in FIG. 7F. FIGS. 7D–7F illustrate placement of the heart valve within the aortic valve 52. In this embodiment, the expandable ball valve 74 is axially displaced in a longitudinal direction inside the implantable structure 68 to open and close the heart valve. In particular, the expandable ball valve member 74 is restricted at distal and proximal ends 78 of the implantable structure 68 to ensure that the valve member 74 remains within the implantable structure 68.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. An expansible prosthetic heart valve comprising:
   an implantable structure comprising a tubular framework which is expansible from a first reduced diameter to a second enlarged diameter and having a flow path therethrough, the tubular framework having:

a strength sufficient to maintain luminal patency when the framework is expanded within a valve of the heart; and a plurality of radial protrusions, the protrusions extending radially about the tubular framework so as to anchor the tubular framework within the valve of the heart when the tubular framework is expanded therein;

a flexible membrane positionable in the flow path for permitting flow in a first direction and substantially resisting flow in a second direction; and a membrane support positionable in the flow path and affixed to the implantable structure, wherein the membrane support comprises at least one rib member extending across the flow path, wherein the membrane support is fixed relative to the flexible membrane so that the flexible membrane flexes away from the membrane support including the at least one rib member during opening of the flow path in the first direction, wherein the flexible membrane is attached to a portion of the membrane support.

2. An expansible valve as in claim 1, wherein the membrane support comprises a circular wire frame.

3. An expansible valve as in claim 1, wherein the membrane support and the implantable structure define an integral framework.

4. An expansible valve as in claim 1, wherein the flexible membrane has a substantially circular shape.

5. An expansible valve as in claim 1, wherein the flexible membrane has a substantially conical shape.

6. An expansible valve as in claim 1, wherein the flexible membrane comprises at least one leaflet.

7. An expansible valve as in claim 1, wherein the flexible membrane comprises expanded polytetrafluoroethylene or biological materials.

8. An expansible valve as in claim 1, wherein the implantable structure is fixed with respect to the flexible membrane during opening and closing of the flow path.

9. An expansible valve as in claim 1, wherein the framework comprises a plurality of struts, wherein at least three struts are longer than the remaining struts.

10. An expansible valve as in claim 1, wherein the radial protrusions extend circumferentially and longitudinally about an outer surface of the framework.

11. An expansible valve as in claim 1, wherein the implantable structure or membrane support is covered with a layer of expanded polytetrafluoroethylene or biological materials.

12. An expansible valve as in claim 1, wherein at least a portion of the implantable structure, flexible membrane, or membrane support is coated with an anti-thrombogenic substance.

13. An expansible valve as in claim 1, wherein the implantable structure, flexible membrane, and membrane support are expandable from a first reduced profile configuration to a second enlarged profile configuration.

14. An expansible valve as in claim 1, wherein the flexible membrane is attached to a central or peripheral portion of the membrane support.

15. An expansible valve as in claim 1, wherein the at least one rib member comprises a plurality of radial ribs.

16. A method for implanting an expansible prosthetic heart valve, the method comprising:

providing a prosthetic heart valve an expansible structure, a flexible membrane, and a membrane support having at least one rib member, wherein the flexible membrane is attached to a portion of the membrane support, and wherein the expansible structure comprises a tubular framework;

implanting the expansible structure within a valve of the heart by expanding the expansible structure from a first reduced diameter to a second enlarged diameter, wherein a flow path extends therethrough;

positioning the fexible membrane in the flow path for permitting flow in a first direction and substantially resisting flow in a second direction; and positioning the membrane support in the flow path, wherein the at least one rib member extends across the flow path so as to support the flexible membrane against the flow path in the second direction, wherein the flexible membrane flexes away from the membrane support including the at least one rib member during opening of the flow path in the first direction.

17. A method as in claim 16, wherein the valve of the heart comprises a mitral valve, aortic valve, pulmonary valve, or tricuspid valve.

18. A method as in claim 16, wherein the membrane support is affixed to the expansible structure, and wherein the membrane support and expansible structure are fixed with respect to the flexible membrane during opening and closing of the flow path.

19. A method as in claim 16, wherein implanting is carried out by percutaneously passing a catheter endoluminally through an anatomic passageway to a valved anatomic site within the heart.

20. A method as in claim 16, wherein implanting further comprises aligning the structure within the intraluminal site with at least three long struts.

21. A method as in claim 16, further comprising anchoring the expansible structure with a plurality of hooks.

22. A method as in claim 16, wherein positioning further comprises expanding the membrane support from a first reduced profile configuration to a second enlarged profile configuration.

23. A method as in claim 16, wherein positioning further comprises expanding the flexible membrane from a first reduced profile configuration to a second enlarged profile configuration.

24. A method as in claim 16, wherein the flexible membrane is attached to a central or peripheral portion of the membrane support.

25. A method as in claim 16, wherein the at least one rib member comprises a plurality of radial ribs.

26. A method as in claim 16, wherein the implanted tubular framework has a strength that maintains luminal patency of the valve of the heart.

27. A method as in claim 16, wherein flex of the implanted tubular framework is sufficiently limited during opening and closing of the prosthetic heart valve to inhibit failure.

* * * * *